(12) United States Patent
Scheckel et al.

(10) Patent No.: US 10,478,540 B2
(45) Date of Patent: Nov. 19, 2019

(54) PUMP, IN PARTICULAR A BLOOD PUMP

(71) Applicant: ECP ENTWICKLUNGSGESELLSCHAFT MBH, Berlin (DE)

(72) Inventors: Mario Scheckel, Berlin (DE); Robert Decke, Berlin (DE)

(73) Assignee: ECP ENTWICKLUNGSGESELLSCHAFT MBH, BerlinAmtsgericht Berlin (Charlottenburg) (DE)

( * ) Notice: Subject to any disclaimer, the term of this patent is extended or adjusted under 35 U.S.C. 154(b) by 232 days.

(21) Appl. No.: 15/033,409

(22) PCT Filed: Oct. 31, 2014

(86) PCT No.: PCT/EP2014/073485
§ 371 (c)(1),
(2) Date: Apr. 29, 2016

(87) PCT Pub. No.: WO2015/063277
PCT Pub. Date: May 7, 2015

(65) Prior Publication Data
US 2016/0279310 A1    Sep. 29, 2016

(30) Foreign Application Priority Data
Nov. 1, 2013    (EP) ..................... 13191304

(51) Int. Cl.
*A61M 1/12* (2006.01)
*A61M 1/10* (2006.01)

(52) U.S. Cl.
CPC ........ *A61M 1/1024* (2014.02); *A61M 1/1029* (2014.02); *A61M 1/101* (2013.01); *A61M 1/1008* (2014.02); *A61M 1/1012* (2014.02); *A61M 1/1013* (2014.02); *A61M 1/1034* (2014.02); *A61M 1/122* (2014.02); *A61M 1/125* (2014.02);
(Continued)

(58) Field of Classification Search
CPC .. A61M 1/101; A61M 1/1024; A61M 1/1029; A61M 1/1037
See application file for complete search history.

(56) References Cited

U.S. PATENT DOCUMENTS

| | | |
|---|---|---|
| 6,533,716 B1 | 3/2003 | Schmitz-Rode et al. |
| 7,878,967 B1 | 2/2011 | Khanal |
| 2011/0275884 A1 | 11/2011 | Scheckel |

(Continued)

FOREIGN PATENT DOCUMENTS

| | | |
|---|---|---|
| EP | 2047872 A1 | 4/2009 |
| WO | 2011/003043 A1 | 1/2011 |
| WO | WO-2013/093001 A2 | 6/2013 |

OTHER PUBLICATIONS

International Search Report, PCT/EP2014/073485, dated Jun. 15, 2015 with English translation (20 pages).

*Primary Examiner* — Allen Porter
(74) *Attorney, Agent, or Firm* — White & Case LLP

(57) ABSTRACT

The present invention relates to a pump, in particular a blood pump having a proximal and a distal end and a pump housing arranged therebetween, a driveshaft arranged in an interior of the pump housing along the longitudinal direction, a conveying element arranged on the driveshaft, and a cannula. Here, the pump housing, the shaft arrangement and the conveying element are coordinated with one another in such a way that these guarantee the best possible efficiency and longevity of the pump.

14 Claims, 8 Drawing Sheets

(52) U.S. Cl.
CPC ............ *A61M 2205/0238* (2013.01); *A61M 2205/0266* (2013.01)

(56) References Cited

U.S. PATENT DOCUMENTS

| | | |
|---|---|---|
| 2012/0039711 A1 | 2/2012 | Roehn |
| 2012/0172655 A1 | 7/2012 | Campbell et al. |
| 2013/0053623 A1 | 2/2013 | Evans et al. |
| 2013/0204362 A1 | 8/2013 | Toellner et al. |

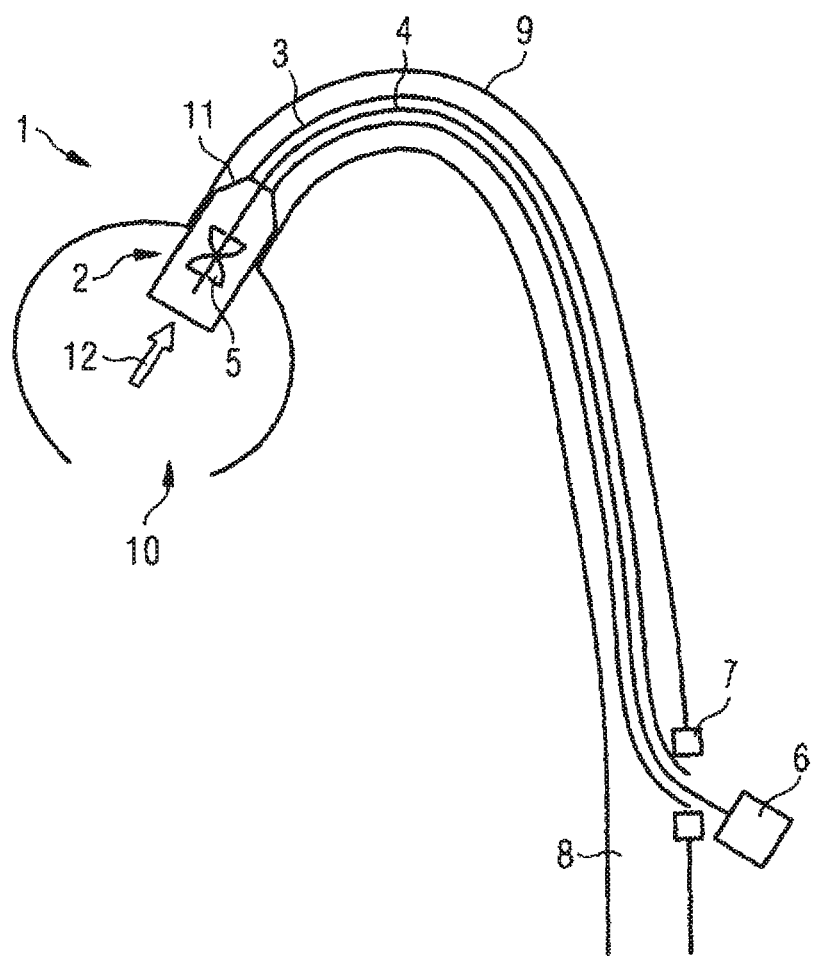

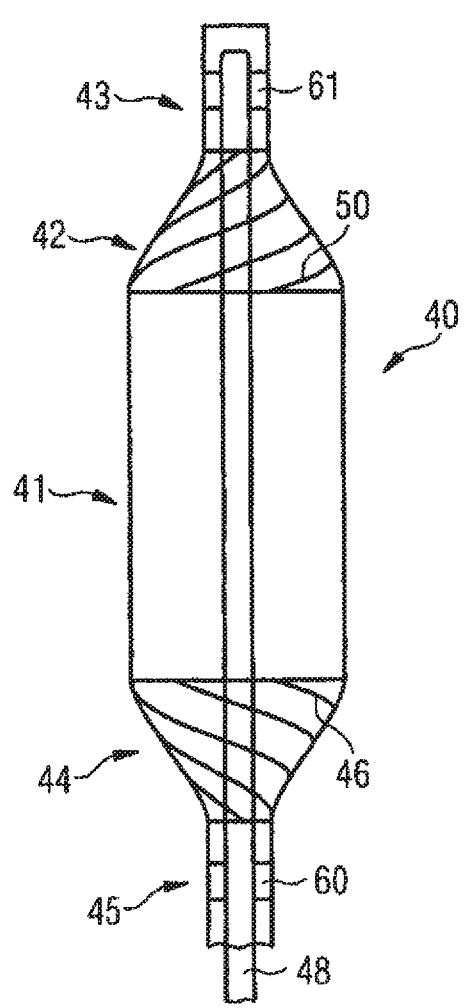
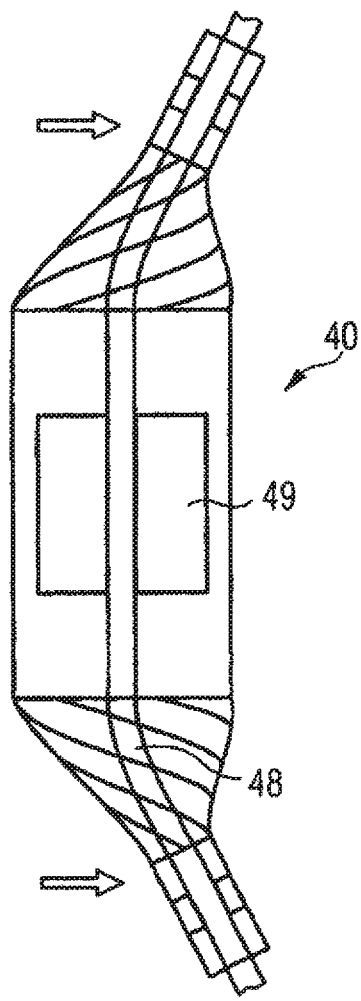

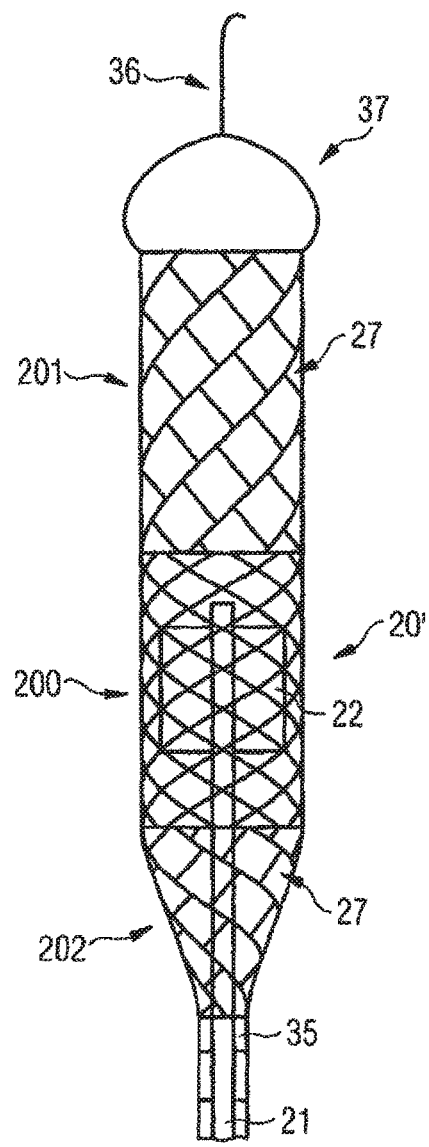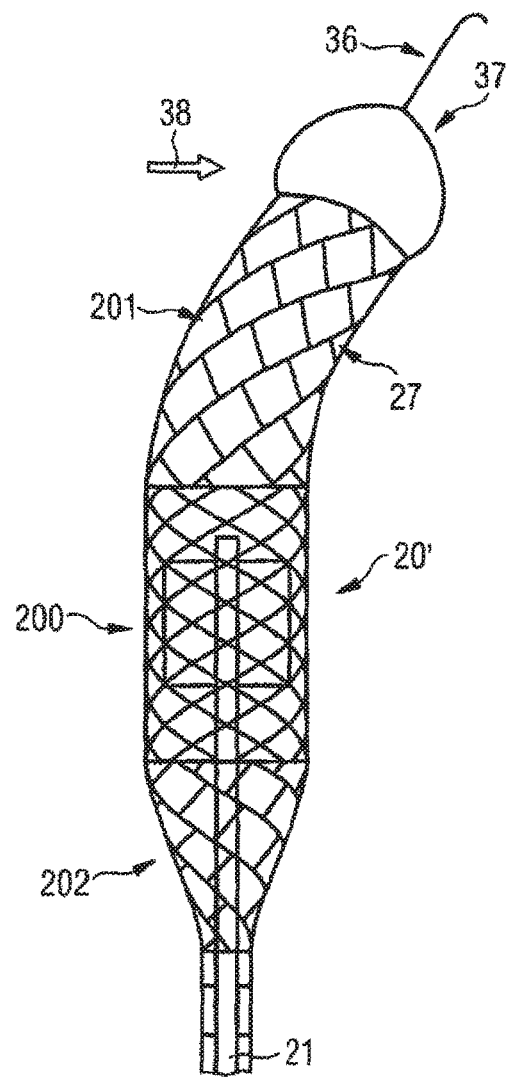

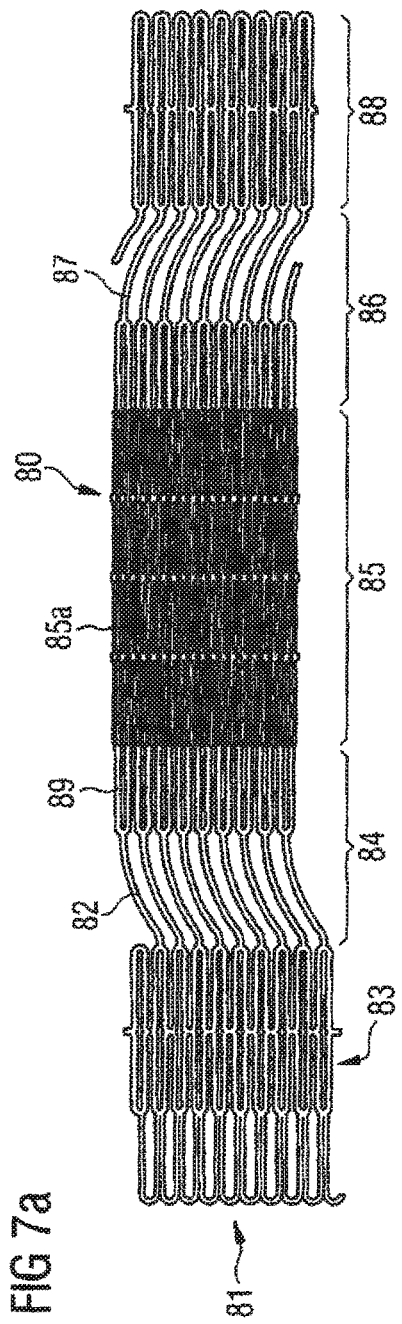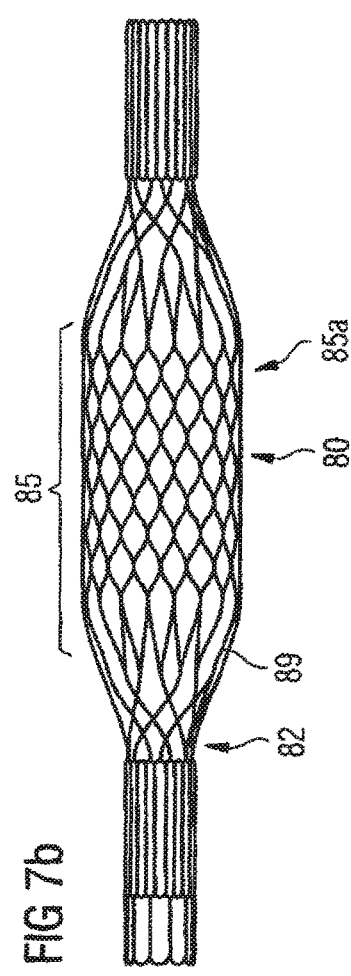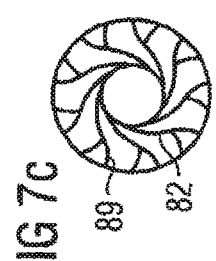

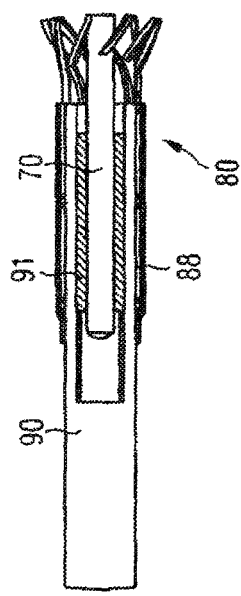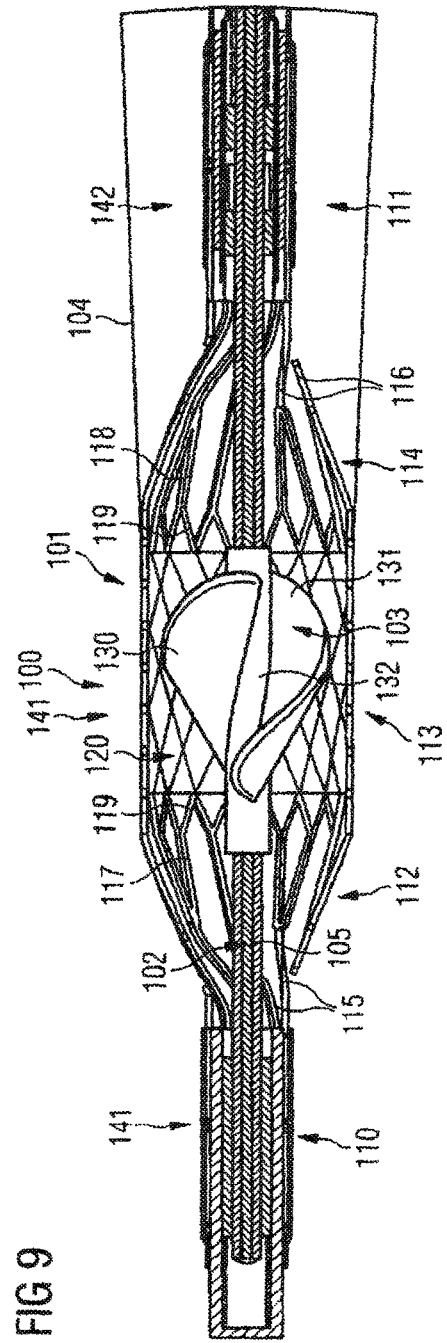

PUMP, IN PARTICULAR A BLOOD PUMP

CROSS-REFERENCE TO RELATED APPLICATIONS

This application is a United States National Stage filing under 35 U.S.C. § 371 of International Application No. PCT/EP2014/073485, filed Oct. 31, 2014, which claims priority to European Patent Application No. 13191304.8, filed Nov. 1, 2013, the contents of all of which are incorporated by reference herein in their entirety. International Application No. PCT/EP2014/073485 was published under PCT Article 21(2) in German.

The invention lies in the field of mechanics, precision mechanics and material technology and relates to a pump or pump arrangement, in particular a blood pump.

In the prior art pumps are known that have a proximal and a distal end and also a pump housing arranged therebetween, a driveshaft arranged in an interior of the pump housing along a longitudinal direction, a conveying element arranged on the driveshaft, and also a cannula or a catheter arranged proximally of the pump housing. Pumps of this type often have a flexible driveshaft, such that the pumps can be guided even at locations that are difficult to access and can implement their pump effect there. One example is a blood pump, which for example is inserted into the left ventricle of the heart through the femoral artery via the aortic arch and remains in the region of the aortic valve. At the proximal end of the pump, i.e. for example at the end of the driveshaft that remains arranged outside the body, the pump may be connected to a motor, which drives the driveshaft and thus the conveying element arranged on the driveshaft, which is now arranged for example in the left ventricle. Blood can thus be pumped from the ventricle into the aorta.

In such pumps it is also known that the pump housing is formed in such a way that it can be transferred at least in part into the cannula or the catheter under application of a force acting at the proximal end of the pump. In other words, by means of the application for example of a tensile force in the region of the proximal end of the driveshaft, the pump housing can be drawn into the cannula and can thus be brought from an expanded state with a larger radial extension into a compressed state with a smaller radial extension. This transfer is provided in particular before the insertion and removal of the pump into and from the body, since the reduced diameter of the pump housing facilitates the navigation of the distal end of the pump within the human body and in particular ensures a minimally invasive passage through the skin. The pump housing is usually made here from a metal, for example a memory-shape metal. Further materials can be used for the pump housing, provided they withstand the mechanical stresses during the compression and the expansion and also meet the medical hygiene standards.

In the case of pumps of this type it is also not unusual for the conveying element, such as a rotor, to comprise at least one foldable or flexible segment, for example in the form of a rotor blade. An example of a rotor of this type is explained for example in U.S. Ser. No. 13/261,565, of which the disclosure is incorporated in its entire scope into this application. Furthermore, U.S. Ser. No. 13/261,100 is likewise incorporated in its entire scope into this application.

With regard to the pump housing, reference is made by way of example to U.S. Ser. No. 13/146,452, which likewise is incorporated in its entire scope into this application.

Reference is also made to U.S. Ser. No. 13/261,256, which is likewise incorporated in its entire scope into this application.

When designing the pump housing, it has proven to be possible to create a portion which in the expanded state of the pump housing winds along a longitudinal axis extending along the driveshaft, around this longitudinal axis as considered from the proximal towards the distal end of the pump, in a spiralled manner around the longitudinal axis. Here, however, a structure extending in a spiralled or helical manner, in particular a spiralled or helical strut, is not to be understood to mean that this must completely surround the longitudinal axis. It is also understood to mean portions of a spiral which form merely a segment of a spiral around the longitudinal axis, i.e. reference may also be made to a curved strut which substantially follows a course of a spiral around the longitudinal axis over a portion.

With the development of pumps of this type the inventors have identified that an advantageous cooperation between the pump housing, the driveshaft and the conveying element is helpful in order to create an efficient blood pump that can be implanted over a relatively long period of time.

This object is achieved by means of a pump according to the features of claim 1, according to the features of claim 14.

In accordance with a first aspect of the invention, the structures extending helically or a structure (singular) extending helically are/is formed in such a way that when the pump housing is transferred from the expanded state into the compressed state a torque directed against a first direction acts on the foldable segment. Here, it should be mentioned that in this application reference is made frequently to a torque acting in a clockwise direction or anticlockwise. More specifically, reference is not made here to the torque, but to the direction of the force generating the torque. The torque is the vector product from the radial position vector directed outwardly from a longitudinal axis and the generating force and thus extends perpendicularly to the generating force. In other words, where reference is made to a torque extending in a clockwise direction, this rather means a torque extending parallel to the longitudinal axis. For the sake of simplicity and improved orientation, however, the direction of the torque is often equated with the direction of the generating force, although this does not correspond to the physical definition.

The portion that comprises the structures extending helically preferably forms merely a limited portion of the pump housing. This portion causes the pump housing to develop a torque when drawn into the cannula, which torque is directed against the direction of the helical winding. The rotor, on account of its form and its flexible or foldable segments, has a tendency to wrap around the driveshaft in a certain direction upon compression of the housing. Since the torque is produced upon compression of the housing, this may likewise act on the foldable segment and therefore urge the foldable segment for example in a folding direction predetermined therefor.

This means that the torque applied by the pump housing assists the natural folding of the flexible segment around the driveshaft and thus counteracts damage at the rotor.

In a first embodiment of the first aspect the foldable segment of the conveying element is formed in such a way that the torque of a rotational direction of the conveying element is equivalent to the conveyance of a fluid from the distal to the proximal end of the pump. In other words the first direction, in which the helical structures extend, is opposite to the rotation of the conveying element in operation when the fluid is conveyed from the distal to the proximal end of the pump when the flexible segments of the conveying element are formed accordingly. Astonishingly, it has been found that both an improvement of the efficiency of the pump is possible as a result, and potential damage of the pump housing can be reduced.

In a further embodiment the foldable segment of the conveying element is created in such a way that the torque is directed opposite to a rotational direction of the conveying element, and in addition the unfolding direction of the at least one foldable segment during the unfolding extends in the first direction. This means that the rotational direction of the conveying element when conveying the fluid from the distal to the proximal end is directed opposite to the unfolding direction of the rotor.

In a further variant the foldable segment of the conveying element may be formed in such a way that the torque is directed opposite to a rotational direction of the conveying element for conveying a fluid from the distal to the proximal end of the pump.

In a further embodiment the unfolding direction of the at least one foldable segment during unfolding is in a direction opposite to the first direction.

In a further embodiment the pump housing is produced from a memory-shape material. Here, the pump housing may be manufactured for example from nitinol.

In a further embodiment, the "austenite finish" ($A_f$) temperature of the pump housing lies below the body temperature of a healthy human, in particular below 30° C. and in particular below room temperature, i.e. below 20° C. It has surprisingly been found that at this $A_f$ temperature the stability and the longevity of the housing can be improved. This is true in particular when the $A_f$ temperature is below room temperature.

In a further embodiment the pump housing comprises a pump-receiving portion and a proximal portion arranged proximally of the pump-receiving portion, wherein an inner diameter of the proximal portion is reduced from a diameter of the pump-receiving portion in the expanded state of the pump housing to a proximal end of the proximal portion. By means of a pump housing of this type the drawing into the cannula is facilitated and assisted on account of the form of the pump housing. Here, a variant of the pump according to the invention is provided in which the helical structures are arranged in the proximal portion.

In an alternative embodiment, the helical structures are arranged in the pump-receiving portion. In a further embodiment the helical structures are arranged both in the proximal and in the pump-receiving portion.

In a further embodiment the pump housing comprises a further, distal portion arranged distally of the pump-receiving portion, the inner diameter of said further, distal portion preferably being reduced from a diameter of the pump-receiving portion in the expanded state of the pump housing to a distal end of the distal portion.

An improved protection of the rotor is thus possible, since the driveshaft can be pivoted, for example in the region of the reduced inner diameter of the distal portion by a further bearing.

In a further embodiment the helical structures are also arranged in the distal portion. Here, the helical structures can be wrapped or wound against the first direction. In this embodiment the helical structures assist the formation of a torque both in the proximal and in the distal portion, said formation of a torque being initiated over the entire pump housing between the proximal and distal portion, but the torque causing a deflection or twisting of the helical elements merely in the region of the proximal and distal portion. In a variant the helical structures in the proximal and distal region are formed in such a way that the torque is directed in the same direction proximally and distally and/or the proximal and distal torque is of identical magnitude. This is comparable in an analogy with the wrapping of a sweet in a sweet wrapper, wherein the sweet can be unwrapped from the wrapper by holding and at the same time pulling both ends. By way of example, the driveshaft is thus prevented from twisting and the driveshaft is thus protected against damage.

In a further embodiment the driveshaft is pivoted alternatively or additionally in a region of a proximal end of the pump housing.

In a second aspect of the invention an unfolding direction of the at least one flexible element when transferring the pump housing from the compressed into the expanded state is provided against the rotational direction of the conveying element when a fluid is conveyed from the distal to the proximal end of the pump, irrespective of helical structures. In this case, as in the first aspect of the invention, the movement of the outer end of the segment of the conveying element, as considered radially, is to be understood to mean the unfolding direction.

A further aspect of the invention comprises a pump housing, a driveshaft arranged in an interior of the pump housing along a longitudinal axis, and a conveying element arranged on the driveshaft. The pump housing comprises at least one pump-receiving portion and a proximal portion arranged proximally of the pump-receiving portion, wherein the pump housing can be transferred in a radial direction extending transversely to the longitudinal direction from a compressed state into an expanded state. The driveshaft is pivoted in the region of the proximal end of the pump housing in a proximal bearing.

In this third aspect of the invention the driveshaft is configured in such a way that a bending resistance of the driveshaft in the region of the proximal portion of the pump housing and distally of the proximal bearing corresponds with a bending resistance of the proximal portion of the pump housing. In this way, in the event of any bending, the pump housing and the conveying element are mounted/pivoted substantially concentrically with one another within the pump-receiving portion. In other words the bending line of the pump housing in the proximal portion is harmonised with the bending line of the flexible shaft in the region of the proximal portion, such that a bending moment acting on the distal end of the pump housing induces a similar bend both in the housing and in the shaft. The rotor is thus prevented from colliding with the pump housing on account of different resistances to bending, and destruction of the pump housing or of the rotor itself is also prevented. During the operation of the pump, the movement of the beating heart or of the patient may result in bending moments or forces which may lead, without coordination of the resistances to bending or bending moments, to damage to the rotor or pump housing.

In a variant the bending resistance of the proximal portion of the pump housing is softer compared with the pump-receiving portion. In the region of the proximal portion the flexible shaft is also softer compared with a shaft portion in the pump-receiving portion of the housing.

The bending resistance of the pump housing in the proximal portion may be influenced for example by helical structures. Due to the helical structures, a resilient region which intercepts the mechanical alternating loads on account of differently acting bending moments is created in one exemplary embodiment. Here, in accordance with a variant, the helical structures are to be arranged symmetrically around the longitudinal axis. The helical structures in this way form a helical region which has a spring effect. This spring effect allows the control of the desired bending resistance. In particular, the desired bending resistance can be set via the angle or the spiral course of the helical structures. In order to ensure a fatigue strength of the pump housing, a maximum local distortion at any point of the pump housing is less than 2% in a variant.

In a further embodiment the pump housing also comprises a distal portion distally of the pump-receiving portion, wherein the driveshaft in the region of the distal end of the pump housing is pivoted in a distal bearing and a bending resistance of the driveshaft in the region of the distal portion and proximally of the distal portion is coordinated in such a way with a bending resistance of the distal portion that when the pump housing bends the conveying element is arranged substantially concentrically within the pump-receiving portion. Here, the driveshaft for example may additionally be pivoted in the region of the distal end of the pump, such that the driveshaft is fixed between a proximal and a distal bearing. Because the driveshaft in the region of the distal and proximal portion of the pump housing has a bending resistance that corresponds with a bending resistance of the pump housing in the proximal or distal portion, it is possible to ensure the substantially concentric mounting of the rotor in the pump housing.

In a further embodiment the pump housing is formed in such a way that it is coordinated with a rigidity of a catheter, for example in the distal or proximal end of the pump region. If the catheter is too rigid, strong deformations are introduced into the pump housing, however if the catheter is too soft the position of the housing during operation is not secured, such that in neither case can reliable operation of the rotor in the pump housing be ensured. By coordinating the rigidity of the pump housing with the rigidity of the catheter, the concentric mounting of the rotor in the pump-receiving portion is ensured here even during operation of the pump.

In order to influence the bending resistance of the shaft, a hollow shaft may be used inter alia, which is provided in the region of the pump-receiving portion with a core. In addition, the core may extend as far as the distal bearing and the proximal bearing.

In the pump arrangements described in this application different external force effects and bending alternating loads act in reality on the driveshaft, the pump housing, a pigtail arranged distally of the pump housing, and where applicable on bearing elements of the catheter or of the blood pump arrangement. External force effects and bending alternating loads can be transferred to the catheter for example by an inner wall of the heart, against which the catheter may be abutted or supported (for example via what is known as a pigtail tip), by pulsatile pressure changes or flow changes of the blood within a heart chamber or a blood vessel, such as the left or right ventricle or the aorta, and/or by a change in position or posture of the body, in particular by a torso movement or a (leg) movement in the vicinity of a puncture site. In spite of these loads, blood can be conveyed with the proposed catheter and the proposed blood pump arrangement over relatively long periods of time, for example over hours, days or even weeks, even at high rotational speeds of the pump rotor, for example in the above-mentioned rotational speed range, for example as in the above-described use of the blood pump arrangement.

It is noted that the features specified in the claims dependent on independent claim 1 can also be combined with the second and third aspect of the invention.

Further aspects will be explained on the basis of the following figures.

In the figures:

FIG. 1 shows a schematic overview of a pump arrangement;

FIGS. 4a and 4b show an exemplary embodiment of a corresponding bending resistance between pump housing and driveshaft;

FIGS. 5a and 5b show further embodiments of a pump housing and a driveshaft with corresponding bending resistances;

FIGS. 7a to 7c show embodiments of a pump housing;

FIG. 8 shows an embodiment of a distal end of the pump housing with catheter attached therein;

FIG. 9 shows an illustration of a pump arrangement with a coordinated combination of pump housing and driveshaft for harmonisation of the bending line.

Figure 2A:
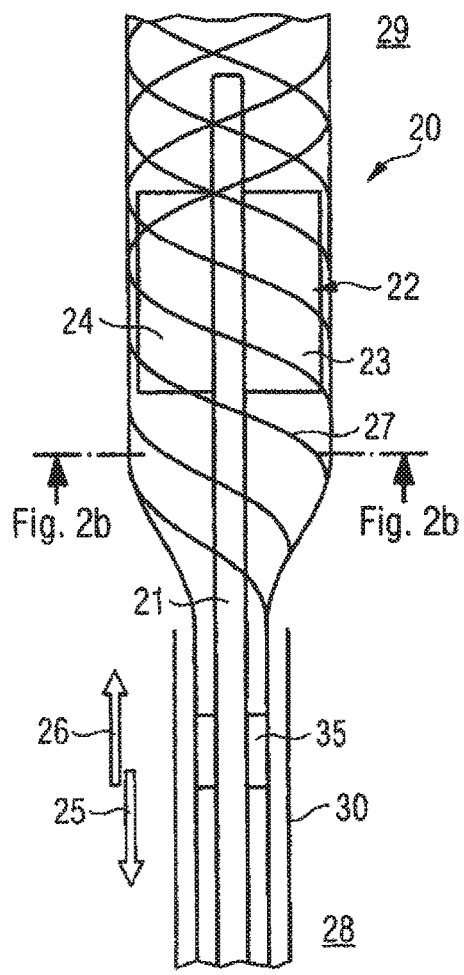
FIGS. 2a to 2d show a variant of a pump housing with conveying element arranged therein on a driveshaft, which is pivoted merely proximally.

A schematic overview of a pump arrangement 1 is provided on the basis of FIG. 1. The pump arrangement 1 comprises a pump housing 2 with a cannula or a catheter 3, in which a driveshaft 4 is arranged. A conveying element 5, which is driven via the driveshaft 4 with a motor 6 attached at the proximal end of the driveshaft, is located in the region of the pump housing 2. The pump including the driveshaft 4 is introduced here via a port 7, for example through the femoral artery 8 and the aortic arch 9, into a heart ventricle 10, such that the pump housing to comes to lie in the region of the aortic valve. The rotor 5 is formed here in such a way that blood is conveyed in the direction 12 from the ventricle into the aorta, i.e. from the distal end of the pump to the proximal end of the pump.

Figure 2C:
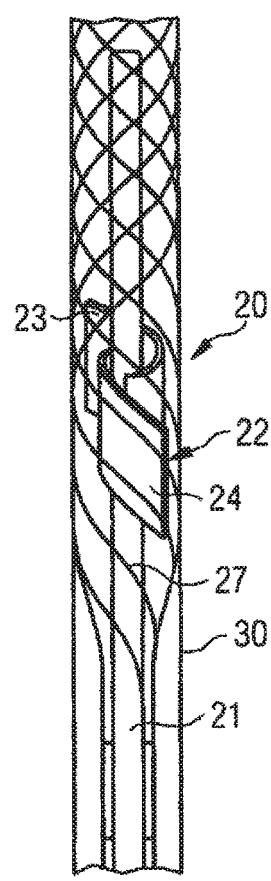

Various interactions between the housing, the driveshaft, the conveying element and the cannula will be explained on the basis of FIGS. 2a to 2d. In FIGS. 2a and 2c the pump housing 20 is illustrated in longitudinal section in the expanded state (FIG. 2a) and the compressed state (FIG. 2c). Corresponding cross sections can be found in FIGS. 2b and 2d.

Figure 2B:
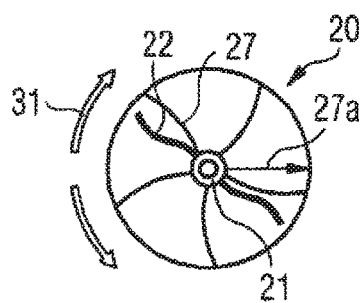

The driveshaft 21 is arranged in the pump housing 20 with the conveying element 22 located on the driveshaft. In the present example the conveying element comprises two flexible segments 23 and 24, which are embodied as rotor blades. The pump housing 20 transfers from the expanded state into the compressed state by pulling the driveshaft in the pulling direction 25, which is parallel to the longitudinal direction 26 of the pump housing. A cross section is illustrated in FIG. 2b for illustration of the pump housing in the illustration of FIG. 2a. It can be seen that the pump housing 20 is arranged substantially concentrically around the driveshaft 21. In the section illustrated here, the struts 27 extending helically as helical structures can be seen and widen from the proximal to the distal portion in the radial direction 27a. The struts extend from the proximal end of the pump housing 28 to the distal end of the pump housing 29, in an anticlockwise direction. By comparison, the conveying element 22 is also shown, of which the flexible segments convey the fluid. This can also be seen in the plan view of FIG. 2a. Alternatively to the multiplicity of struts, another helical structure may also be selected, for example a multiplicity of struts that form a helical line, i.e. structure, on account of their arrangement.

Figure 2D:
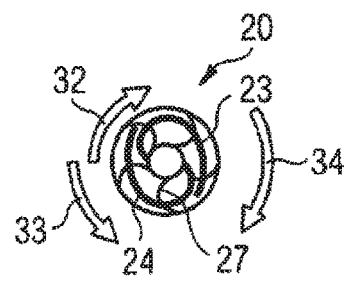

If the pump housing 20 is now drawn into the cannula 30 from the expanded state illustrated in FIG. 2a into the compressed state by pulling in the pulling direction 25, the helical elements produce a torque 31, which acts in the clockwise direction. It is thus opposed in the course of the helical struts and attempts to counteract the twisting of the helical struts, although no visible change of the housing is discernible. As a result of the torque, the segments 23 and 24 are acted on such that the segments 23 and 24, as illustrated in FIG. 2d, wrap around the driveshaft 21 in the folding direction 32 with the torque 31. Accordingly, the rotor unfolds as the pump housing is slid out from the cannula 30 in the longitudinal direction in the unfolding direction 33.

In the example illustrated here the subsequent rotational direction of the rotor is in the rotational direction 34, which is opposite to the unfolding direction. A further unfolding of the rotor at higher rotational speeds can be provided as a result, inter alia. In other variants, however, it is possible to select the rotational direction to be consistent with the unfolding direction. A higher rotational speed here causes an easy folding of the rotor in the folding direction 32.

In the present example the driveshaft is made of a nickel-cobalt alloy, such as 35NL T® or MP35N®. The cannula is for example formed from a catheter made of a material known from the prior art, such as silicone or polyurethane. The pump housing may be fabricated for example from nitinol. Here, in the present example the $A_f$ temperature of the pump housing lies at approximately 15°, such that the $A_f$ temperature lies below room temperature. This has advantages in terms of the stability of the pump housing. In the following example the driveshaft is pivoted merely by a proximal bearing sleeve 35. With regard to the used materials for the rotor, the materials described in U.S. Ser. No. 13/261,565 can be used, for example.

In the example illustrated in FIG. 2 the struts arranged helically extend both in the proximal portion of the pump housing, which lies proximally of the conveying element 22, and in the region of the pump-receiving portion, which lies in the region of the conveying element 22.

A variant of a combination of pump housing, conveying element and driveshaft is shown by way of example in FIGS. 3a to 3d.

A difference between the embodiments of FIG. 2 and FIG. 3 is, inter alia, that the driveshaft in the embodiment of FIG. 3 is pivoted both in a distal end and in the region of a proximal end of the pump housing.

Figure 3A:
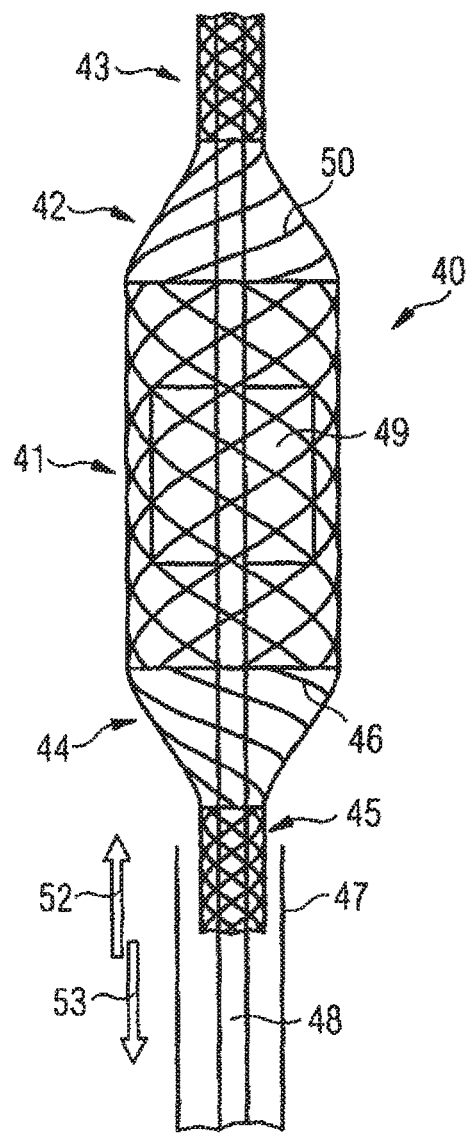
FIGS. 3a to 3d show a variant of a pump with a pump housing and a conveying element mounted on a driveshaft, wherein the driveshaft is pivoted distally and proximally.
Figure 3C:
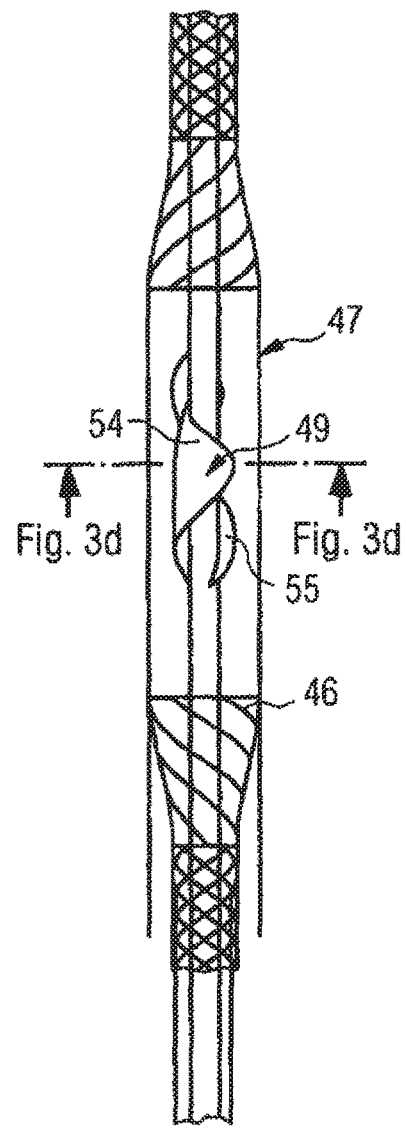
Figure 3B:
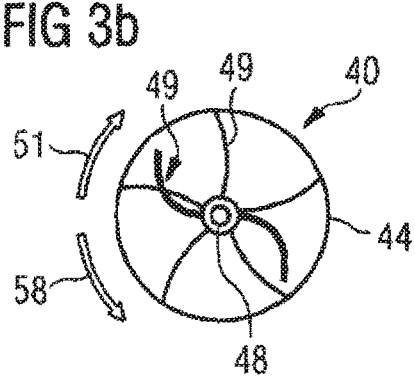
Figure 3D:
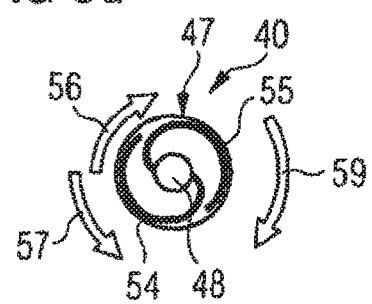

The pump housing 40 illustrated in FIG. 3a comprises a pump-receiving portion 41, a portion 42 arranged distally of the pump-receiving portion, and a distal end portion 43 arranged distally of the distal portion. The pump housing also comprises a proximal portion 44 arranged proximally of the pump-receiving portion and an end portion 45 arranged proximally of the proximal portion. The pump housing 40 has, in the proximal portion 44 and the distal portion 42, helical struts 46, which are shown by way of example in FIG. 3b. The struts extend here from the proximal end of the pump to the distal end of the pump, in an anticlockwise direction. A cannula 47 is additionally shown in FIG. 3a, which cannula encases the driveshaft 48 as it passes through the aortic arch and the bodily vessels. A rotor 49 is additionally arranged on the driveshaft in the region of the pump-receiving portion 41 of the housing and serves to convey blood from the distal to the proximal end. It can be seen on the basis of FIG. 3b that the helical struts 46 extend in the proximal portion 44 in an anticlockwise direction and from the inside out (i.e. the distal end of the end portion 45) out (i.e. towards the proximal end of the portion 41), whereas the helical struts 50 in the distal portion 42 extend in a clockwise direction and from the outside in. As a result, when the distal end portion 43 and the proximal end portion 45 are grasped and pulled at both portions in opposite directions, a torque extending in a clockwise direction acts on the pump-receiving portion 41. This mechanism is effective also when the pump housing is drawn into the cannula. In a manner corresponding to FIG. 2a, the pump in FIG. 3a illustrated in the expanded state. If a tensile force 53 directed against the longitudinal direction 52 is now effective, the diameter of the pump housing is reduced on the one hand in the portions 41, 42 and 44, and at the same time the torque 51 acting in a clockwise direction is induced. On account of the reduction of the diameter during the collapse, the pump housing 40 interacts with the conveying element 49 or flexible segments 54 and 55 thereof. On account of their form and their orientation, the flexible segments 54 and 55 have a folding direction 56 in the direction of the torque. In this way, the flexible segments 54 and 55 are wound around the driveshaft 48 in the folding direction 56. If the pump housing is now transferred from the compressed configurations in FIG. 3c into the expanded configuration of FIG. 3a, the rotor unfolds in the unfolding direction 57, which coincides with the spiral direction 58 of the helical struts. In the present example the rotor 48 then turns in the direction 59 in order to guide the blood from the distal to the proximal end of the pump.

The embodiment shown in FIG. 3 corresponds to a "sweet wrapping", since the spirals defining the course of the helical struts rotate in opposite directions in the distal and in the proximal portion. As a result a torque is introduced in the pump-receiving portion 41 merely in the distal and proximal portion 42 and 44, however the torque acting in the distal and proximal end portions 43 and 45 is reduced. Since bearings (not illustrated) for the driveshaft 48 are located in the distal and proximal end portions, the torque of the pump housing is transmitted where appropriate to the driveshaft when the pump housing 40 is transferred from the expanded into the compressed state.

The aspects of the corresponding bending resistance of the pump housing and of the shaft will be discussed on the basis of FIGS. 4a and 4b and also FIGS. 5a and 5b.

A pump arrangement corresponding to that of FIG. 3 is illustrated in FIGS. 4a and 4b. In particular, the pump housing 40 comprises the portions 41 to 45 described with reference to FIG. 3, and a driveshaft 48, which is held proximally in a first bearing 60 and a distal bearing 61. Helical struts 46 and 50 are disposed in the distal and proximal portions 42 and 44 respectively. If a bending moment is now applied to the pump housing 40, as illustrated in FIG. 4b, the helical struts 46 and 50 cause, inter alia, the pump housing to bend on account of their symmetrical arrangement around the driveshaft, said bending corresponding to a corresponding bending of the driveshaft in the distal and proximal portions 42 and 44 respectively. Here, the shaft may be softer for example in the aforementioned regions than in the region of the pump-receiving portion 41. The stiffening in the pump-receiving portion is additionally reinforced by the rotor itself or the rotor hub. As a result, as can be seen in FIG. 4b, the conveying element 49 remains substantially concentric within the pump-receiving portion, even under bending loads. By way of example on account of the thickness of the struts, the selected angle of the helical struts, and also the number and arrangement of the struts, a corresponding bending moment can be adapted to the bending resistance of the shaft in the corresponding region. Here, the bending moment is the sum of the product from the generating force and the corresponding force arm over all acting forces. Here, the force arm is the distance from a bearing point. By way of example, a point in the region of the proximal bearing may be selected as bearing point.

In FIGS. 5a and 5b a corresponding situation is illustrated, wherein the pump arrangement here corresponds substantially to the pump arrangement of FIG. 2. However, the pump housing 20 in this case has a rigid, pump-receiving portion and a distal portion 201 disposed distally of a pump-receiving portion 200, which distal portion has helical structures 27. The helical structures 27, which may be generated on account of a conductor-like arrangement of a multiplicity of struts and connections thereof or by segmental rotation of strut structures, are configured in such a way that the bending resistance of the pump housing in the distal portion 201 is softer than in the pump-receiving portion 202. Bending moments acting on the pigtail 36 can thus also be absorbed by the distal portion in addition to the distal transition structure 37, which for example may be constructed from 4 struts.

The bending moment 38 (FIG. 5b) thus does not act on the pump-receiving portion, such that the driveshaft lies substantially concentrically within the pump-receiving portion, even when bending moments are applied. The pump-receiving portion 200 is more rigid, wherein measures for increasing the bending resistance will be explained in one of the subsequent exemplary embodiments.

The pump housing may optionally also comprise a proximal portion 202 having helical structures 27 in order to compensate for an effective bending moment and in order to facilitate the compression of the pump housing.

Figure 6A:
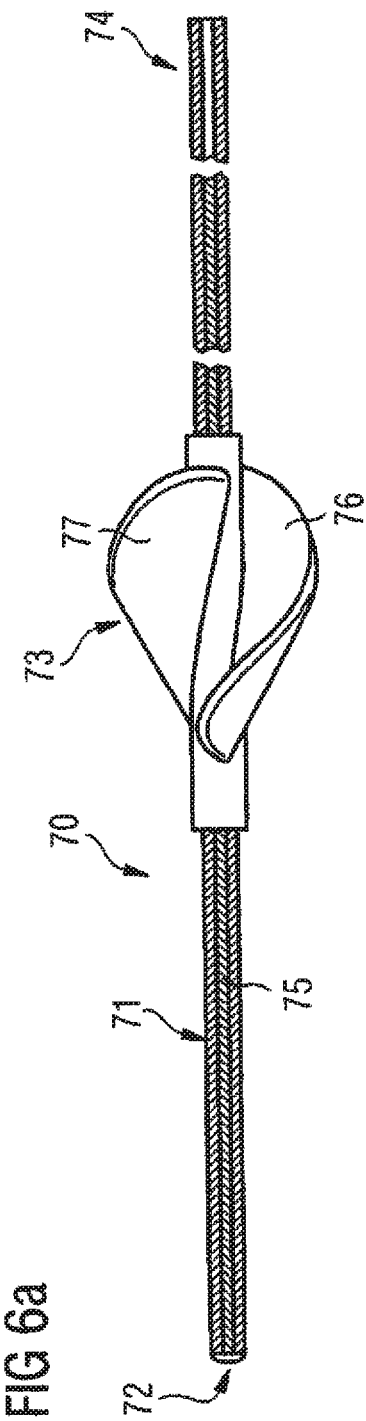
FIGS. 6a and 6b show embodiments of a driveshaft with core and rotor.
Figure 6B:
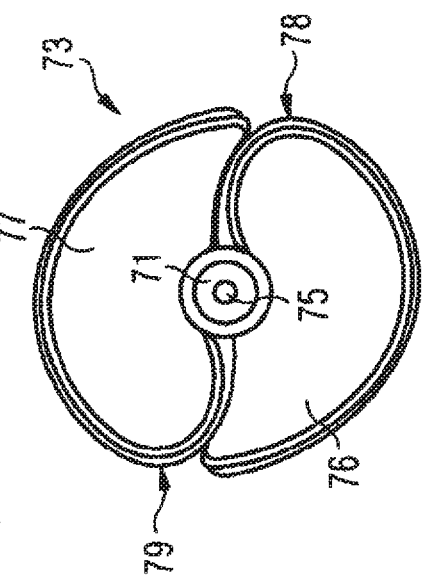

Further details of the various aspects of the invention will be discussed on the basis of FIGS. 6a and 6b. The shaft arrangement 70 comprises the driveshaft 71 with a distal end 72, a conveying element 73, and a proximal end 74, which for example can be coupled to a motor using a coupling element. In the region of the conveying element 73, the driveshaft 71 is reinforced by a core 75, wherein the core extends between the distal end 72 and a region proximally of the conveying element 73. The conveying element 73 comprises two flexible segments 76 and 77, which cause a fluid to be conveyed from the distal to the proximal end with a rotational direction of the conveying element in a clockwise direction, as considered from the proximal to the distal end. In FIG. 6b a cross section of the rotor from the proximal end to the distal end is illustrated. Here, the form of the flexible segments 76 and 77 can be seen in greater detail. The folding direction of the rotor when the pump housing (not illustrated) is drawn into the cannula is in a clockwise direction, i.e. the points 78 and 79 are transported radially inwardly and in a clockwise direction. Accordingly, the rotor unfolds as the conveying element is slid out from the catheter in an anticlockwise direction. Therefore, in a variant, the illustrated conveying element or the shaft arrangement 70 is provided with a housing formed in such a way that this produces a torque in a clockwise direction when the pump housing is transferred from the expanded into the compressed state.

Here, the core 75 may produce an improved rigidity compared with the other regions of the hollow driveshaft 71. Here, the core may have different rigidities from its distal to its proximal end, such that for example the bending resistance proximally and/or distally of the conveying element is reduced compared with the rigidity of the core in the region of the conveying element. The corresponding rigidity of the shaft in the region of the conveying element, however, may also be achieved by a corresponding design (or coordination) of the rotor hub.

Further details of a pump housing will be explained on the basis of FIGS. 7a to 7c. In FIG. 7a the pump housing illustrated in FIG. 7b has been cut along a fictitious separation line, unrolled and pressed flat. However, in one embodiment the pump housing, as illustrated in FIG. 7a, is first cut out for example by means of a laser. Here, the cutting-out can be performed within a tube mould. The form illustrated in FIG. 7b is then provided by means of an annealing process in a mould. The pump housing 80 in FIG. 7a, likewise unrolled, has at its proximal end 81 the proximal end portion 83, which extends as far as the helical elements 82. A short region before and after the helical struts 82 here defines the proximal portion 84. The pump-receiving portion 85 has a lattice design, in which the struts interconnected in a lattice shape have points of contact with one another. Similarly to the proximal portion 84, the distal portion 86 has helical struts 87, which are obviously directed to the struts 82 in terms of their spiral direction. At the distal end there is disposed a distal end portion 88, in the region of which for example the driveshaft can be pivoted in a catheter or pigtail. The angle at which the helical elements 82 extend from the proximal end portion to the pump-receiving portion may be between 20 and 40°, for example. Similarly, the angle of the struts 87 may also be 20 to 40° (but in the opposite direction).

In their embodiment, the two angles are oppositely directed, as illustrated in FIG. 7. If the pump housing 80 is now joined together, as indicated above, the pump housing in the expanded state as illustrated in FIG. 7b is produced. It can be clearly seen that in the region of the proximal and distal portions 84 and 86 respectively there is a widening of the inner diameter from the proximal to the distal end and vice versa. The pump-receiving portion 85 here has the greatest inner diameter in order to attain a high efficiency when conveying the fluid. A cross section of the pump housing 80, as considered from the proximal end to the distal end, is shown in FIG. 7c, wherein it can be clearly seen that the struts 82 run in an anticlockwise direction. The supporting struts 89 are also illustrated and transition to the lattice struts 85a of the pump-receiving portion.

The distal end portion 88 of the pump housing 80 is illustrated on the basis of FIG. 8. Here, a catheter 90 is inserted into the distal end portion 88 and comprises, inter alia, a bearing sleeve 91, in which the distal end of the shaft arrangement 70 is pivoted. Here, the bearing may consist for example of a ceramic, whereas the shaft may be constructed from the previously described materials.

In FIG. 9 a longitudinal section through a pump arrangement 100 is shown, which comprises a pump housing 101, a driveshaft 102, and a rotor 103 arranged on the driveshaft. An outflow tube 104 is also illustrated. In the distal end region 110 of the pump housing, this is connected to a catheter formed as a pigtail (not illustrated). Here, the mounting of the driveshaft 102 in the distal end portion corresponds substantially to the mounting explained on the basis of FIG. 8.

In the region of the proximal end portion 111 there is disposed a proximal bearing/pivoting 112 of the driveshaft, which comprises both a radial bearing and an axial bearing. This bearing is explained in greater detail in the European patent application published as EP 2868289 A1 (having the internal file reference 137EP 2457). That application is incorporated fully into this application.

Between the distal and proximal end portions of the pump housing 101 there are disposed the distal portion 112, the pump-receiving portion 113, and the proximal portion 114. Here, both the distal and the proximal portion have helical struts 115 and 116 respectively, which transition towards the pump-receiving portion into supporting struts 117 and 118 respectively. These supporting struts each split further into struts 119 of the pump-receiving portion. On the inner side of the pump-receiving portion there is located a plastics film 120, which is produced in an exemplary embodiment from a polyurethane. This film improves the conveying effect of the rotor 103.

The rotor 103 comprises two flexible rotor blades 130 and 131, which are fastened to a hub 132. In some exemplary embodiments the rotor is a single workpiece made of a plastic, such as polyurethane, for example biresin, or from a silicone or Pebax. For reasons of clarity, the rotor 103 is not shown in a longitudinal sectional illustration.

The rotor 103 is arranged on a driveshaft 102, which is formed as a hollow shaft. Reference is made to the application PMP Ref. 137EP 2457 with regard to further details. The hollow shaft is reinforced by a core 105 between the distal and proximal bearing/pivoting.

When coordinating the bending line of the pump housing with the bending line of the driveshaft, it should be ensured, in the event of a bending moment 140 (or 141 or 142) acting on the pump housing, that the rotor 103 remains substantially concentric in the pump-receiving portion 113, or that the rotor does not contact the inner face of the pump-receiving portion 113. As a first measure the bending resistance of the pump-receiving portion is more rigid in this exemplary embodiment than the bending resistance of the distal or proximal portion. For the sake of simplicity, the bending resistances of the distal and proximal portion are selected symmetrically in the shown exemplary embodiment. A possibility to influence the bending resistance in the pump-receiving portion 113 is constituted by the density and number of the struts 119 in relation to the considered diameter of the housing. In the present example the distal and proximal portions 112 and 114 respectively each have 10 helical struts, which transition into 20 supporting struts 117 and 118 respectively towards the pump-receiving portion. The supporting struts 117 and 118 split again into 40 struts 119, such that the number of struts in the pump-receiving region is greater here by a factor of 4. In other exemplary embodiments this factor may vary between 0.9 and 20. The bending resistance in the pump-receiving portion is in this way greater than in the distal or proximal region.

A further possibility for matching (here: making softer) the bending resistances of the distal and proximal portion compared with the pump-receiving portion is constituted by the change of the geometric dimensions of the struts 115-119. In the present example the struts 115 and 116 are thicker by a factor of 2 to 3 than the struts 119. On account of the factor 4 in the ratio of the number of struts, the proximal and distal portion would otherwise be too soft in some exemplary embodiments if the struts 115-119 were of equal thickness.

A further possibility for matching the bending resistance in the region of the proximal and distal portions is constituted by the selection of the bending angle of the helical struts. In the present example the helical struts wind by an angle of approximately 30° from the distal to the proximal end of the proximal or distal portion. However, the range may also lie in a range from 5° to 90°.

A further possibility is to vary the length of the proximal and distal portion. In a method for matching the bending resistance of the pump housing, the shaft arrangement is first measured, and the above-mentioned parameters of the different portions of the pump housing are then calculated, and a suitable pump housing is then produced.

The bending resistance of the driveshaft may be matched by the rigidity of the hollow shaft, of the core and of the rotor. Since the hollow shaft in some exemplary embodiments may be exposed to strong curvatures, for example in the aortic arch, the hollow shaft must have a bending resistance that allows a curvature of this type and at the same time has a strength so as to be able to operate for as long as possible at high rotational speeds. In some exemplary embodiments the bending resistance of the hollow shaft is therefore adapted primarily to the requirements of the hollow shaft between motor and bearing. However, the rigidity of the core may also be adapted in order to adapt the bending line of the driveshaft to the bending resistance of the pump housing between the proximal and distal bearing.

Furthermore, the material selection and geometry of the rotor 103 causes a stiffening of the driveshaft in the region of the pump-receiving portion 113, such that the driveshaft arrangement with rotor is softer in the region of the distal and proximal portion than in the region of the pump-receiving portion. Further adaptation possibilities will become clear to a person skilled in the art from the comments made here.

In a further exemplary embodiment the pump housing has a helical structure, which occurs as a result of a multiplicity of interconnected struts. Due to the selection of the connection point between two struts, although the struts extend at an incline upwardly or downwardly, a helical structure directed in one direction is produced. The bending resistance of this structure may be matched to the bending resistance of the driveshaft by changes to the thickness, number and length of the structure and by changes to the encompassed angle of the structure.

Further embodiments and variants of the invention will emerge from the combinations specified here and from the combinations apparent to a person skilled in the art.

The invention claimed is:

1. A pump, in particular a blood pump, comprising
a proximal and a distal end and a pump housing arranged therebetween,
a driveshaft arranged in an interior of the pump housing along a longitudinal direction,
a conveying element arranged on the driveshaft, and
a cannula,
wherein the pump housing is formed in such a way that the pump housing can be transferred at least in part into the cannula under application of a force acting at the proximal end of the pump, and in doing so is transferred at least along a radial direction extending transversely to the longitudinal direction from an expandable state into a compressed state; and wherein the pump housing also has at least one portion which in the expanded state comprises structures extending along the longitudinal axis helically around the longitudinal axis and wound in a first direction as considered from the proximal to the distal end of the pump; and
wherein the conveying element comprises at least one foldable segment, wherein the structures extending helically are formed in such a way that a torque directed against the first direction acts on the at least one foldable segment causing it to collapse.

2. The pump according to claim 1, wherein the at least one foldable segment of the conveying element is formed in such a way that the torque is directed in the same direction as a rotational direction of the conveying element for conveying a fluid from the distal to the proximal end of the pump.

3. The pump according to claim 1, wherein the at least one foldable segment of the conveying element is formed in such a way that the torque is directed opposite to a conveying direction of the conveying element for conveying a fluid from the distal to the proximal end of the pump.

4. The pump according to claim 1, wherein an unfolding direction of the at least one foldable segment extends in the first direction during the unfolding.

5. The pump according to claim 1, wherein an unfolding direction of the at least one foldable segment extends in a direction opposite to the first direction during the unfolding.

6. The pump according to claim 1, wherein the pump housing is produced from a memory-shape material.

7. The pump according to claim 1, wherein the pump housing comprises a pump-receiving portion and a proximal portion arranged proximally of the pump-receiving portion, wherein an inner diameter of the proximal portion is reduced from a diameter of the pump-receiving portion in the expanded state of the pump housing towards a proximal end of the proximal portion.

8. The pump according to claim 7, wherein the helical structures are arranged in the proximal portion.

9. The pump according to claim 7, wherein the helical structures are arranged in the pump-receiving portion.

10. The pump according to claim 7, wherein the pump housing comprises a further, distal portion arranged distally of the pump-receiving portion, the inner diameter of said further, distal portion is preferably reduced from a diameter of the pump-receiving portion in the expanded state of the pump housing towards a distal end of the distal portion.

11. The pump according to claim 10, wherein the helical structures are arranged in the distal portion.

12. The pump according to claim 1, wherein the driveshaft is pivoted at least in a region of a proximal end of the pump housing.

13. The pump according to claim 12, wherein the driveshaft is pivoted additionally in a region of a distal end of the pump housing.

14. The pump according to claim 1, wherein the helical structures comprise helical struts.

* * * * *

UNITED STATES PATENT AND TRADEMARK OFFICE
CERTIFICATE OF CORRECTION

PATENT NO. : 10,478,540 B2
APPLICATION NO. : 15/033409
DATED : November 19, 2019
INVENTOR(S) : Scheckel et al.

Page 1 of 1

It is certified that error appears in the above-identified patent and that said Letters Patent is hereby corrected as shown below:

In the Specification

Column 8, Lines 13-14, delete "FIG. 3a illustrated" and replace with --FIG. 3a is illustrated--

Column 9, Line 14, delete "housing 20" and replace with --housing 20'--

Column 9, Line 51, delete "rotor from the proximal" and replace with --rotor 73 from the proximal--

Signed and Sealed this
Eighteenth Day of February, 2020

Andrei Iancu
*Director of the United States Patent and Trademark Office*